United States Patent [19]

Wu

[11] Patent Number: 5,248,668
[45] Date of Patent: Sep. 28, 1993

[54] USE OF PURPUROGALLIN AND GLYCOSIDES THEREOF IN TREATING ISCHEMIA IN MAMMALS

[75] Inventor: Tai W. Wu, Toronto, Canada

[73] Assignee: Wintek Consulting Ltd., Toronto, Canada

[21] Appl. No.: 952,815

[22] Filed: Sep. 28, 1992

Related U.S. Application Data

[63] Continuation of Ser. No. 701,047, May 16, 1991, abandoned.

[51] Int. Cl.⁵ .................. A61C 31/70; A61C 31/12
[52] U.S. Cl. ........................... 514/25; 514/42; 514/681
[58] Field of Search ............. 514/25, 42, 681

[56] References Cited

U.S. PATENT DOCUMENTS 4,181,545  1/1990  Anderson ............... 149/19.9
4,647,532  3/1987  Watanabe ............... 435/28

FOREIGN PATENT DOCUMENTS 0146338  6/1985  European Pat. Off. .
0326987  8/1989  European Pat. Off. .
56-1470  6/1981  Japan .
WOA8803805  7/1989  PCT Int'l Appl. .
WOA9009789  9/1990  PCT Int'l Appl. .

OTHER PUBLICATIONS

Chem Abst. 111(3):17704v of *Jordan*, PCT Int. Appl. WO 8803805 Jun. 2, 1988 Abstract only.
Merck Index, 11th Edition, entry No. 7963 1989.
Free Radical Research Communications, vol. 2, Nos. 1-2, 1986, Kontoghiorghes.
"Natural Immunity and Cell Growth Regulation", vol. 4, No. 5, Sep.–Oct. 1985 Leung.

*Primary Examiner*—Frederick E. Waddell
*Assistant Examiner*—Gregory Hook
*Attorney, Agent, or Firm*—Ridout & Maybee

[57] ABSTRACT

Purpurogallin and its mono- and di-glucosides are useful as cytoprotective agents. Patient-administrable compositions for addition to a patient's blood to minimize oxyradical damage caused by ischemia-reperfusion injury that may result in various surgical procedures, and comprising purpurogallin or glucosides thereof, and uses thereof, are described.

4 Claims, 2 Drawing Sheets

USE OF PURPUROGALLIN AND GLYCOSIDES THEREOF IN TREATING ISCHEMIA IN MAMMALS

This application is a continuation of application Ser. No. 07/701,047, filed May 16, 1991, now abandoned.

FIELD OF THE INVENTION

The present invention generally relates to antioxidants which are biomedically applicable. More particularly, the present invention relates to the oxyradical scavenging properties of purpurogallin and purpurogallin glucosides.

BACKGROUND OF THE INVENTION

Oxygen free radicals, such as the superoxide radical $O_2$ and hydroxyl radical OH are formed by approximately 5% of the oxygen in the bloodstream. Such oxyradicals are highly toxic and can cause irreversible oxidative damage to cells and tissues. When regular blood flow to a living organ or tissue is interrupted, e.g. during organ transplantation, by-pass surgery and the like (the surgical procedure known as ischemia), the reintroduction of oxygen into the tissue leads to a vast increase in superoxide production, leading in turn to the formation of secondary hydroxyl radicals and marked cellular toxicity. The primary source of the excess free radicals produced after ischemia is xanthine dehydrogenase, an enzyme that normally transfers electrons from purine bases to the oxidized form of nicotinamide adenine dinucleotide. During hypoxia this enzyme is rapidly and irreversibly converted to xanthine oxidase, an enzyme that generates large quantities of superoxide by transferring its electrons directly to oxygen.

Oxygen free radicals can attack and damage important biological molecules. Within cellular membranes, OH can initiate a chain reaction known as lipid peroxidation, in which polyunsaturated fatty acids are broken down into water soluble products with consequent disruption of membrane integrity. Peroxidation of membranes may result in cell death due to the release of lysosomal hydrolases into the cytoplasm. Oxygen radicals can produce mutations in DNA and depolymerise hyaluronic acid and related macro molecules.

The body has several defense mechanisms by which oxidative damage can be minimized. One is an enzymatic mechanism which involves superoxide dismutase, which catalyses the combination of two $O_2$ free radicals with hydrogen to form hydrogen peroxide, a less toxic molecule which is eliminated by a peroxidase such as a catalase. Another defence mechanism is provided by natural antioxidants such as vitamin E (tocopherol) with the hydrophobic core of cell membranes, and glutathione and ascorbic acid in the cell water. Such antioxidants are adequate to detoxify most of the superoxide normally produced within the cell. However they cannot cope with the vastly increased superoxide production which occurs when oxygen is reintroduced into a tissue after a period of ischemia.

There is therefore, a need for a therapeutically effective antioxidant in order to prevent or minimize oxyradical damage that may follow surgical procedures, specifically surgery involving ischemia of organs such as the heart, liver and kidney.

BRIEF DISCUSSION OF THE PRIOR ART

Substances which have previously been proposed for use as free radical scavengers to reduce ischemiareperfusion damage included allopurinol, ascorbic acid, dltocopherol, vitamin E and 6-hydroxy-2,5,7,8-tetramethylchroman-2-carboxylic acid (Trolox) - see for example U.S. Pat. No. 4,877,810. Scott et al., J. Am. Oil. Chem. Soc. 51: 200–203 (1974) report the original design of trolox as an antioxidant for preserving food and fats.

The importance of oxygen radicals in the pathogenesis of diseases such as arthritis, inflammation and certain kinds of cancer, and in aging, has also been recognized. See for example Cross et al., Ann. Int. Med. 107: 526–545, 1974. Vitamin E has generally been considered the best, known, natural antioxidant. However, it is not a particularly satisfactory therapeutic antioxidant, especially under emergency conditions, because it is extremely lipophilic and is taken up by cells only slowly.

Purpurogallin is a known compound, described at entry number 7963 of the Merck Index, 11th Edition. Chemically, it is 2,3,4,6-tetrahydroxy-5H-benzocyclohepten5-one, of chemical structure:

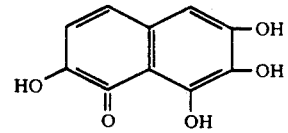

It can be prepared by oxidation of pyrogallol. Its standard uses are as an additive to edible or inedible fats or oils, hydrocarbon fuels or lubricants, to retard oxidation or metal contamination.

U.S. Pat. No. 4,181,545 Anderson, describes the use of purpurogallin and other hydroxy-substituted aromatic compounds as additives in curing systems for polymeric binders for rubber-based solid propellants. They are reported to accelerate the curing action and to complex with metal ions which will otherwise promote oxidative degradation of uncured and cured polymeric systems.

It is an object of the present invention to provide a more efficient, biomedically acceptable antioxidant for use, inter alia, in reperfusion.

SUMMARY OF THE INVENTION

The present invention is based upon the discovery that purpurogallin and its glucosides are unexpectedly useful and efficient as antioxidant and cytoprotective agents in biomedical applications. The efficiency of purpurogallin in such applications is greater than that of previously used antioxidants such as Trolox and ascorbic acid. It is particularly useful in treating a patient's blood following ischemia, to reduce the damage caused by oxidative free radicals on tissues and organs following reperfusion thereof with blood after ischemia Purpurogallin is non-toxic and is persistent, lasting in the bloodstream naturally for several weeks.

The present invention in one aspect provides purpurogallin and its glucosides for use as cytoprotective antioxidant agents.

According to another aspect of the invention, there is provided a composition useful as an antioxidant and cytoprotective agent in mammals, said composition comprising an effective amount of purpurogallin or a glucoside thereof, in association with a physiologically acceptable adjuvant therefor.

From another aspect, the invention provides a method of decreasing the oxidative free radical concentration in mammalian blood, which comprises treating the mammalian blood in vivo with an effective amount of purpurogallin or a glucoside thereof.

BRIEF REFERENCE TO THE DRAWINGS

DESCRIPTION OF THE PREFERRED EMBODIMENTS

Figure 1:
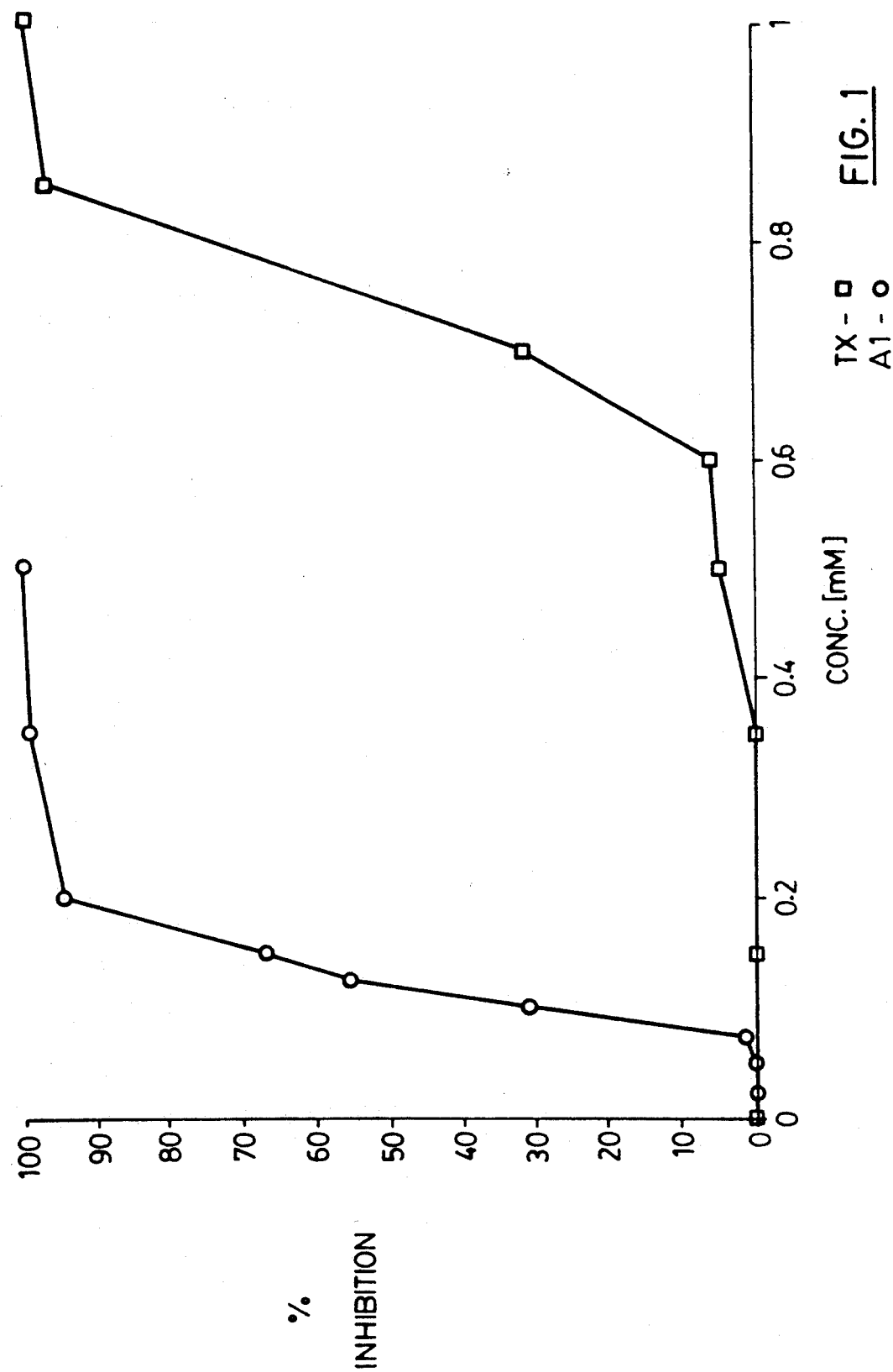
FIG. 1 is a graphical presentation of the results obtained according to Example 1 below.

The preferred process of the present invention is the use of purpurogallin as an antioxidant to reduce organ ischemia—reperfusion injury. For this purpose, an effective amount of the purpurogallin composition, in a suitable physiologically acceptable carrier, in liquid form, is injected into the patient's blood immediately prior to reperfusion of the organ following ischemia, and at a location adjacent to the organ to be reperfused. If such injection takes place adjacent to the organ to be reperfused, lesser amounts of purpurogallin are necessary. Beneficial results can also be obtained by a general injection into the bloodstream of the purpurogallin, at any convenient location, but this is wasteful, and larger quantities of purpurogallin are then necessary. Sometimes, however, in the case of injured patients, injection at other locations is inevitable. Oral administration with a suitable carrier is also possible.

Suitable physiologically acceptable carriers for use with purpurogallin in the present invention include water and saline solution, preferably isotonic saline solution, or any commonly used cardioplegic solution, for ready mixing and compatibility with the blood. Most preferred as the carrier for an injectable purpurogallin solution for administration to a patient is a sample of the patient's own blood, or blood of the patient's type. Such is normally available at the site of the ischemia-involving surgery. It provides ideally biocompatible medium for the patient.

The quantities of purpurogallin to be administered vary based upon the body weight and blood capacity of the patient. In general, it is preferred to provide a patient with from about 0.3 mg-15 mg of purpurogallin per kilogram body weight of the patient, preferably about 0.5-10 mg per kg. For a human adult patient of normal body weight and blood capacity, an amount from about 3 mg-100 mg of the purpurogallin is suitable. Appropriate adjustments can be made to these quantities in proportion to a patient's weight, when administering to children, animals, etc.

The concentration of purpurogallin in the solution to be administered is not critical, and can readily be devised by the administrator. Dilute solutions are usually preferred. It is preferred that the purpurogallin solution be administered to the patient slowly, e.g. over a 10-20 minute period, so that a dilute solution is more easily administered under such conditions. Solutions of concentration 0.1-10 mM, preferably 0.2-5 mM, are suitable. The patient's condition and vital signs should be monitored as the solution is administered, and the rate of administration adjusted if necessary.

DETAILED DESCRIPTION OF THE INVENTION

The present invention is described further in the following non-limiting examples. Unless otherwise stated, all chemicals used were reagent grade, and were supplied by Sigma Chemical Co., St. Louis, Mo., U.S.A. Purpurogallin and Trolox were obtained from Aldrich Chemical Co. AAPH (2,2'-axo-bis-(2-amidinopropane)HCl) was supplied by Polysciences Inc.

EXAMPLE 1

In this example, experiments were conducted with human erythrocytes, subjecting them to free radicals generated by thermal activation of AAPH in a reaction mixture in the absence and in the presence of various amounts of purpurogallin or Trolox, to determine the cytoprotective capability of purpurogallin under these conditions.

Freshly obtained human erythrocytes were washed at least three times in saline with centrifugation at 1500 g×10 min. Then, a 20% suspension of RBC was prepared in the phosphate buffered saline (pH 7.4). (Miki et al., Arch. Biochem. Biophys. 258: 373-380, 1987).

The free radicals were generated by thermal activation of the azo-initiator 2,2'-azo-bis(2-amidinopropane)HCl(AAPH). The reaction mixture (0.5 mL volumes) contained 10% red blood cell (RBC) suspension, AAPH (100 mM final level) and various levels of purpurogallin in 10 mM phosphate buffered saline. The above mixture was incubated at 37° C. for 180 min, while shaking gently. The, 35 μl aliquot of reaction mixture was taken out, diluted in 1.5 mL of saline, and centrifuged (1500 g for 10 min). The absorption of the supernatant at 525 mM was read against a PBA blank. Similarly, the reaction mixture was treated with 1.5 mL of distilled water with sonication for 2 min to obtain complete hemolysis. Percent hemolysis was calculated according to Miki et al. (op. cit.).

FIG. 1, which is a graphical presentation of these results, shows that increasing concentrations of antioxidants (purpurogallin and Trolox) raised the percentage inhibition of red cell lysis. An important index for characterizing the antioxidant efficacy of a cytoprotective agent is the concentration of the agent that elicits 50% inhibition of cells lysis ($IC_{50}$). For purpurogallin, the $IC_{50}$ is 0.12 mM, while that for Trolox is about 0.74 mM. Thus, purpurogallin can protect 50% of the cells from lysis at a concentration that is six times lower than Trolox, so that purpurogallin can be said to be six times as effective as Trolox.

EXAMPLE 2

In this example, experiments were conducted with rat hepatocytes, subjecting them to the action of free radicals in the presence and absence of purpurogallin, at various levels.

Hepatocytes were prepared from male Sprague-Dawley rats (400 g-450 g) according the method of Princen et al. J. Clin. Invest. 78: 1064-1071 (1986), except that the perfusion of the liver was done first with 250 mL of 0.5 mM EGTA and 10 MM HEPES buffer solution (pH 7.4) containing 142 mM NaCl and 6.7 mM KCL via gravity drip at 20 mL/min., then with 100 mL of magnesium-free Hank's Balanced Salt Solution containing 5 mM $CaCl_2$ and 0.05% collagenase according to Seglen, Exp. Cell. Res. 82: 391-398 (1973). All other details were as described previously (Wu et al., Biochem. Cell Biol. 68, 1189-1194, 1990).

Free radical studies were done by removing the cell medium and adding to the cells 3 mL of 0.05M sodium phosphate-buffered saline (PBS) (pH 7.4) containing 66.7 IU/L of xanthine oxidase (XOD) and 2 mM hypoxanthine, the latter two being used to generate oxyradicals. The base for comparing the effect of different levels of purpurogallin was the time taken to cause necrosis in 95% of $10^5$ cells of the same generation in each culture dish. When antioxidant was present, it was added with XOD and hypoxanthine to the cells, and tested blind in randomized triplicates by the evaluator. Purpurogallin solutions were made up with PBS that had been degassed for at least 30 min. Since purpurogallin is partly water-soluble, solutions with 4 mM level of purpurogallin was prepared with brief sonication. The pH was adjusted to 7.40±0.05 after almost complete dissolution of the solid purpurogallin. The controls included PBS containing either cells alone, or PBS with either XOD or hypoxanthine incubated with cells.

Figure 2:
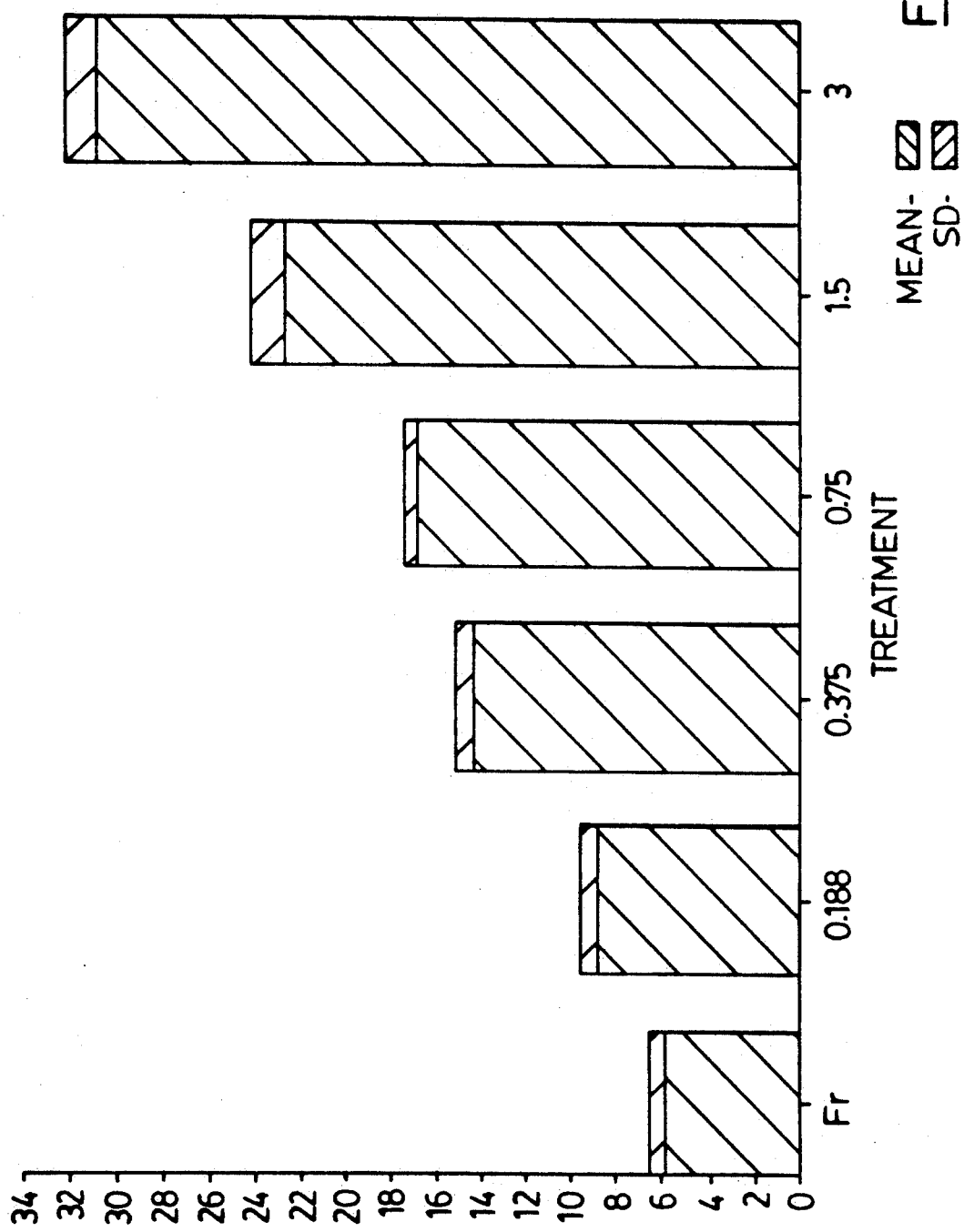
FIG. 2 is a graphical presentation of the results obtained according to Example 2 below.

The results are shown graphically in FIG. 2. On this graph, the vertical axis represents the time, in minutes, taken to necrose 100,000 hepatocytes, and the horizontal axis represents the concentration, in mM, of purpurogallin used in the various tests. Mean values of several experiments at the same level are shown, the statistical analysis having been done using the Student's t test. The data are expressed as means±SD (standard deviation). In comparisons with the control, statistical significance of the data was indicated by a p value<0.05.

FIG. 2 illustrates the dose-dependent effect of purpurogallin on rat hepatocytes. The increasing concentrations of purpurogallin prolonged the time (min) taken to necrose 100,000 hepatocytes that were exposed to oxyradicals. The best cytoprotective effect given by purpurogallin was at the level of 3 mM, which prolonged the time taken to necrose hepatocytes up to 30 min. In the control (i.e. hepatocytes exposed to hypoxanthine and XOD without additive) there was massive necrosis in 100,000 cells in approximately 6 min.

In further studies, culturing the rat hepatocytes and testing for oxyradical damage using purpurogallin and Trolox additives according to the procedure of Wu et al. op. cit., and Clin. Chem. 36: 1172-1173 (abstract), 1990, the results given below in Table I were obtained.

TABLE I

| Concentration (mM) | Mean Survival Time (min) of $10^5$ Rat Hepatocytes After Exposure to Oxyradical | |
|---|---|---|
| | Purpurogallin | Trolox |
| 0.5 | 18 | 12 |
| 1.0 | 20 | 13 |
| 2.0 | 31 | 16 |

In a control experiment, using no additive, the cells survived for about 6.5 minutes when exposed to oxyradicals. This illustrates that, at equivalent concentrations, purpurogallin is clearly more protective of rat hepatocytes than Trolox, which is itself a potent antioxidant derived from vitamin E.

EXAMPLE 3

Human ventricular myocytes were isolated and tested with purpurogallin and Trolox for protection against oxyradical damage using the methods and procedures described by Wu et al., op cit. The results are given below in Table II.

TABLE II

| Concentration (mM) | Mean Survival Time (min) of $10^5$ Rat Myocytes After Exposure to Oxyradical | |
|---|---|---|
| | Purpurogallin | Trolox |
| 0.5 | 14 | 3.5 |
| 1.0 | >60 | 4.5 |
| 1.5 | >60 | 4.8 |
| 3.0 | >60 | 5.3 |

In a control experiment, using no additive, the cells survived for 2 minutes after exposure to oxyradicals.

Each result reported in Table II is the mean of 5-7 closely agreeing replicates. The results demonstrate that purpurogallin is at least an order of magnitude more protective of myocytes than Trolox in this test, especially at levels greater than 0.5 mM.

EXAMPLE 4

Rat kidney mesangial cells were isolated and tested with purpurogallin versus Trolox over the same range of concentrations, for protection against oxyradical damage using methods and procedures described by Wu et al., op cit. Clearly, purpurogallin protects the kidney cells substantially better than Trolox over all the levels examined. The results are given below in Table III.

TABLE III

| mM of Purpurogallin | Mean Time (mins) Survival of Cells Exposed to XOD (66.7 IU/L) and Hypoxanthine (0.5 mM) | |
|---|---|---|
| | Purpurogallin | Trolox |
| 0 (Control) | 5.7 | 5.7 |
| 0.13 | 11.5 | 6.4 |
| 0.25 | 13.4 | 6.6 |
| 0.50 | 16.0 | 7.4 |
| 1.00 | 19.4 | 7.8 |

EXAMPLE 5

In vivo studies were conducted on rat livers, to determine the effectiveness of purpurogallin as a cytoprotectant in partial hepatic ischemia-reperfusion.

There was used the same model as described in Wu et al. Hepatology 13: 575-580, (1991). In essence, the model involves the occlusion of blood vessels supplying to the left lateral, median, and Spigelian lobes of the rate liver by clamping the left portal vein, left hepatic artery and left bile duct. The right portal vein, hepatic artery and bile duct were left intact as an interal shunt. The occlusion was done in Sprague-Dawley rats (0.3-0.4 kg) which had fasted overnight. Approximately 45 seconds before the end of ischemia, either 3 mL of saline (control) or saline containing purpurogallin or Trolox (at the levels specified below) was infused into the animals via the penile vein over a 3 minute period. This was followed by reperfusion for 24 hours. Then, the extent of necrosis (based on wet weight of the liver) was quantified by a well,established histochemical method (Frederiks et al., Exptl. Mol. Path 41: 119-125, 1984).

The results presented below in Table IV show that increasing the dose of purpurogallin from 4.4 to 18 μmoles/kg body weight in the rat model progressively reduces the extent of hepatic necrosis. This is mirrored by the marked increase in organ salvage with increasing dose of the purpurogallin infused. It is noteworthy that the organ salvage at all levels is statistically significant versus the control, and that the effective doses used were all at μmoles for kg body weight.

TABLE IV

EFFECT OF PURPUROGALLIN ON RATS UNDERGOING PARTIAL ISCHEMIA REPERFUSION

| Infusion Dosage | Control Saline Only- no antioxidant) | Purpurogallin (μmoles/kg body weight) | | |
|---|---|---|---|---|
| | | 4.4 | 8.8 | 18 |
| Mean Necrosis (% by weight) | 30.3 | 17.7 | 7.3 | 4.4 |
| ±SD | 11.9 | 4.6 | 4.9 | 1.1 |
| % Salvage of Liver | 0 | 42 | 76 | 86 |
| Number of Rats | 6 | 6 | 6 | 6 |
| P value vs Control | — | <0.05 | 0.005 | 0.001 |

A p value <0.05 is statistioally significant.

EXAMPLE 6

In this example, the cytoprotective effect of purpurogallin in vivo, in heart ischemia-reperfusion in rabbits was examined.

New Zealand white rabbits (3.0-3.5 kg by weight) were anaesthetized with intramuscular injection of Ketamine (35 mg/kg) and Atravet (0.4 mg/kg), and intravenous injection of atropine (0.1 mg/kg).

After shaving the frontal area of the animal, anaesthesia was maintained by performing tracheotomy and ventilating the animal with positive pressure respiration using a Harvard small animal respirator and a gas mixture of 2.5% ethrane (or enflurane) in oxygen. A midline sternotomy was done. The pericardium was opened and the heart was exposed. The main branch of the anterior ventricular coronary artery that supplies blood to a great part of the left ventricle and apex in rabbits (also referred to as the left circumflex coronary artery) was temporarily ligated with a 5-0 silk thread for 1 hour at the site between ½ to ⅔ from apex to the atrioventricular groove. Approximately 1 minute before releasing the occlusion, a 30-ml bolus of 1 mM test solution was injected through the right external jugular vein. In control animals, a 30-mL bolus of normal saline was given instead of the test solution. In all cases, a 3-hour reperfusion followed. After this period, the heart was harvested, stained for enzyme activity with a tetrazolium dye and the areas of necrosis determined by planimetry.

To determine the area at risk, the original ligature in the heart was tightened, and an 22 G angiocath was inserted into the aorta for injection of a 30-mL bolus of Evans' Blue solution. The heart was then sliced transversely into 2 mm thick slices and stained with 1.25% nitro red tetrazolium dye for 30 min. The negative nitrored tetrazolium staining pattern on each slice was traced on a transparent acetate sheet for calculating the necrotic area by computerized planimetry.

The results are given below, in Table V.

TABLE V

| Infustion Dosage | Control Saline (no additive) | Purpurogallin (8.6-10 μmoles/kg body weight) |
|---|---|---|
| Mean % (± SD) organ necrosis in area at risk | 46.6 ± 10 | 11.8 ± 6.2 |
| Mean & organ salvage | 0 | 75 |
| No. of rabbits | 6 | 6 |
| p value vs. control | — | <0.001 |

The 75% mean organ salvage achieved with the relatively low dosage here is statistically and clinically highly significant. This may be the highest myocardial salvage demonstrated with a simple compound under the conditions of this heart model.

EXAMPLE 7

A diglucoside of purpurogallin ($C_{23}H_{28}O_{18}$) was used according to the present invention in methods and procedures as described above, to protect erythrocytes, hepatocytes and myocytes, as well as in the liver and heart models as described above. It performed with similar effectiveness to purpurogallin itself. By high performance liquid chromatography, another (presumably mono-) glucoside was isolated and tested. This compound also performed similarly to purpurogallin. Thus, either purpurogallin or its mono- and diglucosides are superior cytoprotectants, both in cells and in vivo.

I claim:

1. A method of treating ischema in a patient in need of such treatment, which comprises injecting into the bloodstream of said patient an effective amount of a composition of purpurogallin or a glucoside thereof, in association with an aqueous fluid adjuvant therefor.

2. The method of claim 1 wherein the composition contains purpurogallin as the active ingredient thereof.

3. The method of claim 2 wherein there is administered an amount of about 0.3-15 mg purpurogallin per kilogram body weight of the patient.

4. The method of claim 2 wherein there is administered an amount of from 0.5-10 mg purpurogallin per kilogram body weight of the patient.

* * * * *

UNITED STATES PATENT AND TRADEMARK OFFICE
CERTIFICATE OF CORRECTION

PATENT NO. : 5,248,668
DATED : September 28, 1993
INVENTOR(S) : Tai-Wing Wu

It is certified that error appears in the above-identified patent and that said Letters Patent is hereby corrected as shown below:

At column 2, between lines 25 and 30, the structural chemical formula should be changed from the six:six fused ring structure there appearing to the seven:six fused ring structure of the following formula:

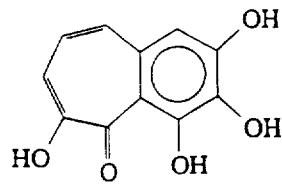

Signed and Sealed this

Seventeenth Day of May, 1994

Attest:

BRUCE LEHMAN

Attesting Officer   Commissioner of Patents and Trademarks